United States Patent
Neumann

(10) Patent No.: US 12,430,151 B2
(45) Date of Patent: Sep. 30, 2025

(54) METHODS AND SYSTEMS FOR PROVIDING ALIMENTARY COMBINATIONS IN A PACKET-BASED GRAPHICAL USER INTERFACE GENERATED USING DISTANCE METRICS

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 1221 days.

(21) Appl. No.: 17/216,126

(22) Filed: Mar. 29, 2021

(65) Prior Publication Data
US 2021/0373921 A1 Dec. 2, 2021

Related U.S. Application Data

(63) Continuation-in-part of application No. 16/886,623, filed on May 28, 2020, now Pat. No. 10,983,674.

(51) Int. Cl.
*G06F 9/451* (2018.01)
*G06F 3/0483* (2013.01)
(Continued)

(52) U.S. Cl.
CPC ............ *G06F 9/452* (2018.02); *G06F 3/0483* (2013.01); *G06F 3/04845* (2013.01); *G06N 7/01* (2023.01);
(Continued)

(58) Field of Classification Search
None
See application file for complete search history.

(56) References Cited

U.S. PATENT DOCUMENTS

| 9,934,530 B1 | 4/2018 | Iacono et al. |
| 10,366,436 B1 | 7/2019 | Kumar et al. |

(Continued)

OTHER PUBLICATIONS

Elsweiler et al., Exploiting Food Choice Biases for Healthier Recipe Recommendation, SIGIR'17, Aug. 7-11, 2017, ACM 2017; pp. 575-584 (Year: 2017).*

(Continued)

*Primary Examiner* — Alan Chen
(74) *Attorney, Agent, or Firm* — Caldwell Intellectual Property Law

(57) ABSTRACT

A system for providing alimentary combinations in a packet-based graphical user interface generated using distance metrics is disclosed. The system includes a computing device designed and configured to receive user classification data, wherein the user classification training data includes a plurality of elements correlating user data entries to user set identifiers. The computing device is configured to receive at least an element of user data, train a user classifier as a function of the user classification training data using a machine learning algorithm. The computing device is configured to classify the at least an element of user data to a user set identifier, set a non-alimentary ordering criterion default parameter as a function of the user set identifier, and order an alimentary combination as a function of the non-alimentary ordering criterion. A method of providing alimentary combinations in a packet-based graphical user interface generated using distance metrics is also disclosed.

20 Claims, 5 Drawing Sheets

(51) Int. Cl.
| | |
|---|---|
| *G06F 3/04845* | (2022.01) |
| *G06N 7/01* | (2023.01) |
| *G06N 20/00* | (2019.01) |
| *G06Q 30/0601* | (2023.01) |
| *H04L 67/10* | (2022.01) |

(52) U.S. Cl.
CPC ......... *G06N 20/00* (2019.01); *G06Q 30/0641* (2013.01); *H04L 67/10* (2013.01)

(56) References Cited

U.S. PATENT DOCUMENTS

| | | | |
|---|---|---|---|
| 2016/0063734 A1* | 3/2016 | Divakaran ............. | G06V 10/50 382/110 |
| 2016/0171514 A1* | 6/2016 | Frank .................... | G06Q 30/02 705/7.29 |
| 2018/0260883 A1 | 9/2018 | Iacono et al. | |
| 2019/0228856 A1* | 7/2019 | Leifer ................. | G06F 16/9035 |

OTHER PUBLICATIONS

Trattner et al., Food Recommender Systems Important Contributions, Challenges and Future Research Directions, arXiv: 1711.02760v2 [cs.IR] Nov. 10, 2017; Total pp. 16 (Year: 2017).*

Yang et al., Yum-Me: A Personalized Nutrient-Based Meal Recommender System, ACM Transactions on Information Systems, vol. 36, No. 1, Article 7, Publication date: Jul. 2017; Total pp. 31 (Year: 2017).*

Gao et al., Hierarchical Attention Network for Visually-aware Food Recommendation, ACM Transactions on Information Systems, vol. 36, No. 1, Article 7, Publication date: Jul. 2017; Total pp. 12 (Year: 2019).*

* cited by examiner

METHODS AND SYSTEMS FOR PROVIDING ALIMENTARY COMBINATIONS IN A PACKET-BASED GRAPHICAL USER INTERFACE GENERATED USING DISTANCE METRICS

CROSS-REFERENCE TO RELATED APPLICATIONS

This continuation-in-part application claims the benefit of priority of U.S. Non-Provisional Patent Application Ser. No. 16/886,623 filed on May 28, 2020 and entitled "METHODS AND SYSTEMS FOR PROVIDING ALIMENTARY COMBINATIONS IN A PACKET-BASED GRAPHICAL USER INTERFACE GENERATED USING DISTANCE METRICS," which is incorporated by reference herein in its entirety.

FIELD OF THE INVENTION

The present invention generally relates to the field of network communication. In particular, the present invention is directed to methods and systems for providing alimentary combinations in a packet-based graphical user interface generated using distance metrics.

BACKGROUND

Existing solutions for selection of a best fit for alimentary provisioning based upon physiological data dictates have generally avoided dealing with the multiplicity of possible solutions by limiting sources or possible selections. This can lead to frustration and under-utilization, which can negate many of the advantages of such solutions.

SUMMARY OF THE DISCLOSURE

In one aspect, a system for providing alimentary combinations in a packet-based graphical user interface generated using distance metrics includes a computing device designed and configured to receive user classification data, where the user classification training data includes a plurality of elements correlating user data entries to user set identifiers. The computing device is configured to receive at least an element of user data, train a user classifier as a function of the user classification training data using a machine learning algorithm. The computing device is configured to classify the at least an element of user data to a user set identifier, set a non-alimentary ordering criterion default parameter as a function of the user set identifier, and order an alimentary combination as a function of the non-alimentary ordering criterion.

In another aspect, a method of providing alimentary combinations in a packet-based graphical user interface generated using distance metrics includes receiving, by computing device, user classification training data, where the user classification training data includes a plurality of elements correlating user data entries to user set identifiers. The method includes receiving, by the computing device, at least an element of user data, training, by the computing device, a user classifier as a function of the user classification training data using a machine learning algorithm. The method includes classifying the at least an element of user data to a user set identifier, setting, by the computing device, a non-alimentary ordering criterion default parameter as a function of the user set identifier, and ordering, by the computing device, an alimentary combination as a function of the non-alimentary ordering criterion.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, embodiments disclosed herein provide alimentary combinations to client devices that are ordered according to criteria including intake requirements as specified by subject-specific alimentary instruction sets. Additional criteria, user-specified and/or selected by default, may be applied to generate ordering. Display according to ordering may be accomplished by a graphical user interface that configures a client device. Data interface may be performed using application programmer interface (API) technology or other data exchange. Embodiments may make use of packet-based transmission and protocols to transfer data and graphical user interface between devices.

In its practical application, the invention enables a user to have a default ordering criterion based on the user set group that the user belongs to. The classification of users is done by training the user classifier using machine learning algorithms. Based on this classification the invention assigns the user a user set identifier and create a criterion for ordering for the user.

Figure 1:
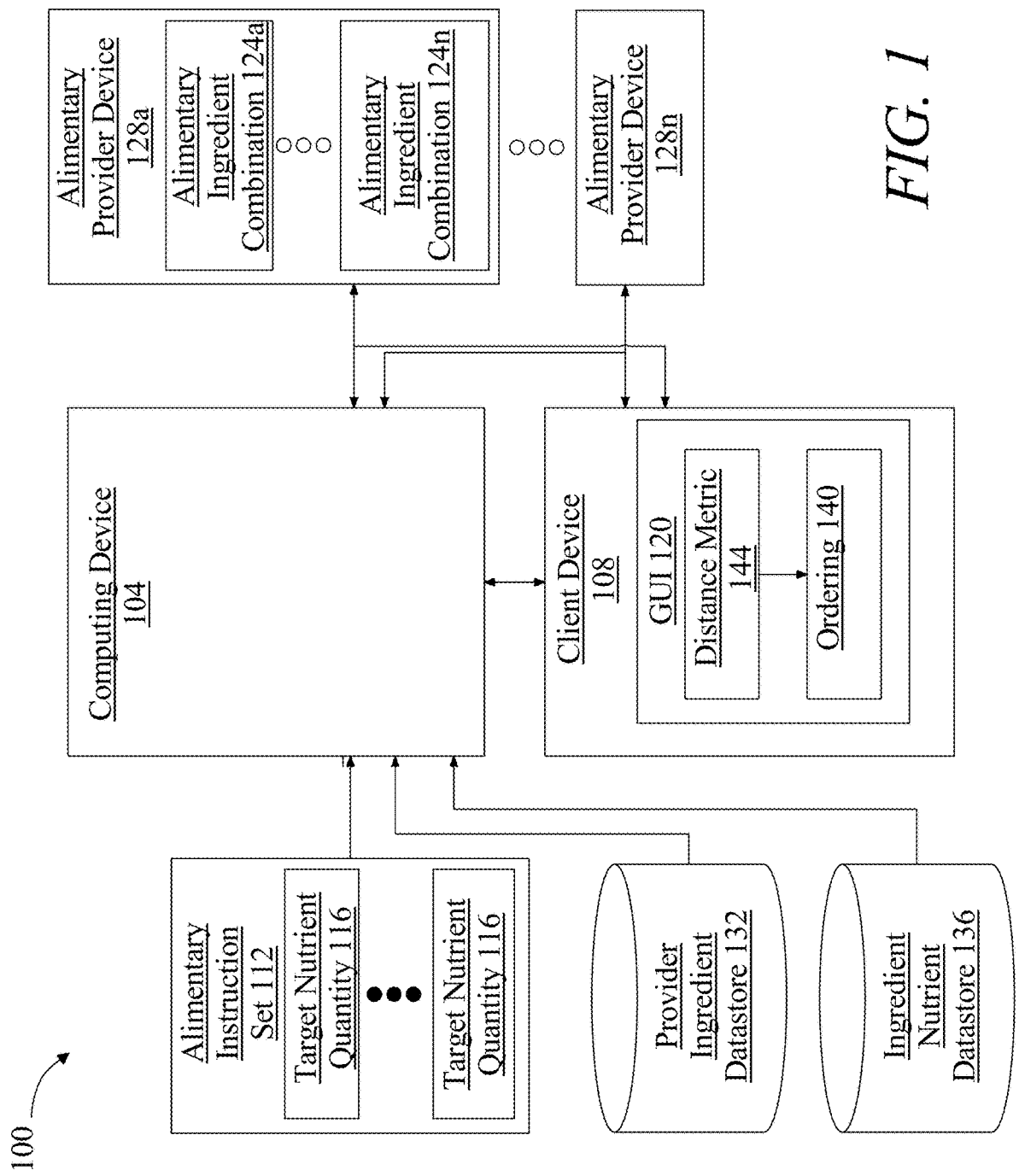
FIG. 1 is a block diagram of an exemplary embodiment of a system for providing alimentary combinations in a packet-based graphical user interface generated using distance metrics.

Referring now to FIG. 1, an exemplary embodiment of a system 100 for providing alimentary combinations in a packet-based graphical user interface generated using distance metrics is illustrated. System includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker, in an embodiment, this may enable scalability of system 100 and/or computing device 104.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to receive a client device identifier. A "client device identifier," as used in this disclosure, is an element of data that may be used to identify a client device 108 operated by a user, such as a user that is searching for alimentary combinations such as meals, recipe kits, or the like; client device 108 may be implemented in any way suitable for implementation of computing device 104. Client device identifier may include a network location and/or address such as a uniform resource locator (URL), internet protocol (IP address), or the like. Client device identifier may alternatively or additionally include any textual string associated with client device 108, and/or with user, which is unique within system 100. Uniqueness within system may be determined at a moment of assigning client device identifier, by checking whether a prospective textual string has been assigned to another client device 108 and/or user, where checking may be performed by querying a database of client identifiers and rejecting prospective textual string upon encountering a matching string that has already been assigned. Alternatively or additionally, client device identifier may include an identifier that is statistically unique, such as a universally unique identifier (UUID) and/or globally unique identifier (GUID). Receipt of client device identifier may be accomplished by receipt of account information from client device 108; alternatively or additionally, computing device 104 may identify client device 108 using IP geolocation or other device fingerprinting techniques, which may or may not be supplemented by account information and/or followed by solicitation thereof With continued reference to FIG. 1, computing device may communicate with client device 108, a plurality of client devices 108, and/or one or more additional devices as described in further detail below using packet-based communication protocols such as without limitation transfer control protocol-internet protocol (TCIP), hypertext transfer protocol (HTTP), secure HTTP (HTTPS), file transfer protocol (FTP), or the like. Network communication may be performed over any network, according to any protocol that may occur to a person skilled in the art upon reviewing the entirety of this disclosure.

Still referring to FIG. 1, computing device 104 is configured to retrieve an alimentary instruction set 112 including a plurality of target nutrient quantities 116 as a function of the client device identifier. Retrieval may include, in an embodiment, identification of a user operating client device 108; for instance, a user operating client device 108 may provide login credentials, and/or may be a sole account holder using client device 108, enabling identification of user by identification of client device 108. As used in this disclosure, an "alimentary instruction set" is a list or other collection of target nutrient quantities 116. As used in this disclosure, a "target nutrition quantity" is a quantity of a given nutrient that alimentary instruction set 112 recommends user to consume; target nutrient quantities 116 nutritional recommendations for a user, including recommendations of foods, nutrients, ingredients, and/or quantities thereof, that a user should consume for improved and/or optimal constitutional state. Quantities may include numbers representing a maximal amount to be consumed, a minimal amount to be consumed, and/or a precise amount that is determined to be ideal. Quantity may be zero for a nutrient that a user should not receive, and/or for a nutrient having no positive result; for instance, a user who is diabetic may be recommended a quantity of zero for glucose, sucrose, or the like.

In a non-limiting embodiment, and further referring to FIG. 1, computing device 104 may provide alimentary instruction set 112 by receiving training data, recording at least a biological extraction from a user, training a machine-learning process using the training data, and, generating the at least an alimentary instruction set 112 as a function of biological extraction and using the machine-learning process. "Training data," as used herein, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and continuing to refer to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 and/or another device may correlate any input data as described in this disclosure to any output data as described in this disclosure.

Still referring to FIG. 1, A "machine learning process," as used in this disclosure, is a process that automatedly uses a body of data known as "training data" and/or a "training set" to generate an algorithm that will be performed by a computing device 104/module to produce outputs given data provided as inputs; this is in contrast to a non-machine learning software program where the commands to be executed are determined in advance by a user and written in a programming language. Generation of alimentary instruction set 112 using machine learning may be implemented, without limitation, as described in U.S. Nonprovisional application Ser. No. 16/502,835, filed on Jul. 3, 2019, and entitled "METHODS AND SYSTEMS FOR ACHIEVING VIBRANT CONSTITUTION BASED ON USER INPUTS," the entirety of which is incorporated herein by reference. Alternatively or additionally, alimentary instruction set 112 may be received from user or other person.

With continued reference to FIG. 1, computing device 104 is configured to transmit a graphical user interface 120 to a client device 108 using an electronic transmission protocol, which may include any transmission protocol as described above. Graphical interface is configured to cause a user device to display a plurality of alimentary combinations 124a-n. Graphical user interface 120 may configure client device 108 to display data output fields including text, images, or the like describing alimentary combinations 124a-n, data input fields such as text entry windows, drop-down lists, buttons, checkboxes, radio buttons, sliders, links, or any other data input interface that may capture user interaction via event handlers and/or polling, as may occur to persons skilled in the art upon reviewing the entirety of this disclosure. Graphical interface may be provided, without limitation, using a web browser, a native application, a mobile application, or the like. An "alimentary combination," is defined for the purposes of this disclosure as a combination of ingredients that an alimentary provider and/or alimentary provider device 128a-n indicates may be provided, for instance and without limitation in the form of a meal. An "alimentary provider," as used in this disclosure, is a person or entity that prepares alimentary products such as meals, food items, and/or drinks, including without limitation a restaurant, a food delivery service, or the like.

Still referring to FIG. 1, ingredients in alimentary combinations 124a-n may include any ingredient or ingredients, where "ingredients" are defined as any ingredient in any alimentary product. In an embodiment, each alimentary provider device 128a-n may indicate a time period, such as a date range, during which each ingredient and/or alimentary combination is available, a geographic region within which each ingredient and/or alimentary combination is available, or the like; alternatively or additionally, each alimentary provider device 128a-n may solely indicated current availability of each ingredient and/or alimentary combination, and/or report only ingredients and/or alimentary combinations 124a-n that are available from an alimentary provider associated with the alimentary provider device 128a-n at the time that transmission occurs. Computing device 104 may store received provider ingredients and/or alimentary combinations 124a-n in a provider datastore 132. Provider datastore 132 may include any data structure for ordered storage and retrieval of data, which may be implemented as a hardware or software module. A provider datastore 132 may be implemented, without limitation, as a relational database, a key-value retrieval datastore such as a NOSQL database, or any other format or structure for use as a datastore that a person skilled in the art would recognize as suitable upon review of the entirety of this disclosure. A provider datastore 132 may include a plurality of data entries and/or records as described above. Data entries in a provider datastore 132 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a provider datastore 132 may reflect categories, cohorts, and/or populations of data consistently with this disclosure. Provider datastore 132 may be located in memory of computing device 104 and/or on another device in and/or in communication with system 100.

With continued reference to FIG. 1, computing device 104 may group provider ingredients and/or alimentary combinations 124a-n within provider datastore 132 according to a geographical region in which the provider ingredients are available, a time period during which the provider ingredients and/or alimentary combinations 124a-n are available, and/or any other category that may be defined by data associated with any provider ingredient and/or alimentary combination as described in this disclosure. Provider ingredients and/or alimentary combinations 124a-n may be grouped in provider datastore 132 according to identifiers of alimentary provider device 128a-ns, and/or associated alimentary providers, that transmitted provider ingredients and/or alimentary combinations 124a-n; in other words, computing device 104 and/or other devices in and/or communicating with system 100 may be able to query provider datastore 132 using an identifier of an alimentary provider and receive in return a list of ingredients and/or alimentary combinations 124a-n currently available to that provider and/or that will be available to that alimentary provider within a given time period and/or at a particular location.

Still referring to FIG. 1, processes as described in this disclosure may be accomplished, in part, by comparison of provider ingredients and/or ingredients in alimentary combinations 124a-n to instruction ingredients. "Instruction ingredients," as used in this disclosure, are ingredients associated with alimentary instruction set 112. Computing device 104 may identify one or more instruction ingredients using an ingredient nutrient datastore 136, which may be implemented using any datastore suitable for use as provider datastore 132. Ingredient nutrient datastore 136 may associate each ingredient of a plurality of ingredients with one or more nutrients contained in the ingredient, as well as amounts of each such nutrient available per a given quantity of the ingredient, such that querying ingredient nutrient datastore 136 using one or more nutrients provided in alimentary instruction set 112 may return a list of ingredients containing the one or more nutrients; query may be implemented as a compound query, that returns ingredients containing selected combinations of nutrients as well as a single query returning any ingredients containing a single nutrient, or the like. Such ingredients may be transmitted to each alimentary provider device 128a-n, permitting alimentary provider device 128a-n and/or a user thereof to indicate each ingredient, of the instruction set ingredients, that alimentary provider is able to use and/or procure. In an embodiment, this may enable alimentary providers to indicate not only ingredients that they currently have in stock, but also ingredients they are able to acquire in a timely manner. Computing device 104 may receive from each alimentary provider device 128a-n, a plurality of matching ingredients. In an embodiment, alimentary provider device 128a-ns may provide both a list of ingredients currently offered, as described above, and a set of selections of instruction ingredients as described above. Computing device 104 may identify plurality of instruction ingredients as a function of the target nutrient quantities 116 using ingredient nutrient datastore 136.

With continued reference to FIG. 1, graphical user interface 120 configures client device 108 to receive, from at least an alimentary provider device 128a-n, a plurality of alimentary combinations 124a-n. An alimentary provider device 128a-n may include any device suitable for use as computing device 104, as described above, which is operated by an alimentary provider as defined above. Graphical user interface 120 may configure client device 108 to receive plurality of alimentary combinations 124a-n from at least an alimentary provider device 128a-n, either directly or through computing device 104, where receipt through computing device 104 signifies transmission from the alimentary provider device 128a-n or devices to computing device 104, which may then transmit the alimentary combinations 124a-n to the client device 108. At least an alimentary provider device 128a-n may include a plurality of alimentary provider device 128a-ns. Transmitting graphical user interface 120 to client device 108 may include remotely configuring the at least an alimentary provider device 128a-n to transmit the graphical user interface 120 to the client device 108; for instance a client-side program generated and/or provided by computing device 104 may extract and/or capture data from alimentary provider device 128a-n, and/or receive such data from a user thereof. Alternatively or additionally, an application programmer interface API may be provided to alimentary provider device 128a-n, having one or more fields for extraction and/or exchange of data from alimentary provider device 128a-n and/or applications, programs, and/or modules operating thereon; data extracted, received, and/or exchanged may include alimentary data such as alimentary combinations 124a-n, ingredients, and/or nutrients, and/or non-alimentary data as described in further detail below. Client-side program and/or API may cause alimentary provider device 128a-n to transmit any such data to client device 108 and/or graphical user interface 120, either directly or through computing device 104.

Still referring to FIG. 1, graphical interface configures client device 108 to generate an ordering 140 of the plurality of alimentary combinations 124a-n according to a distance metric measuring each alimentary combination against the plurality of target nutrient quantities 116. An "ordering," as used in this disclosure, is an order and/or ranking in which and/or or according to which alimentary combinations 124a-n are displayed; for instance, an ordering 140 may associate each alimentary combination with a quantity associated with a numerical field, permitting alimentary combinations 124a-n to be sorted according to magnitude of such quantities. There may be multiple orderings 140, which may be computed concurrently or sequentially according to one or more distance metrics and/or distance metrics computed using criteria such as alimentary and/or non-alimentary data as described in further detail below; concurrently present orderings 140 may be stored such that user entries or other modifications specifying different criteria for orderings 140 as described in further detail below may trigger deployment of stored orderings 140, permitting rapid redisplay of data in accordance therewith even in the absence of computing resources and/or network connectivity. In an embodiment, generation of distance metric from target nutrient quantities 116 may be accomplished by measuring a distance metric from alimentary combinations 124a-n to all of target nutrients. Alternatively, computing device 104 may match alimentary combinations' nutrients to a subset of target nutrients. For example, and without limitation, where user has already consumed some of target nutrients and/or some portion of one or more target nutrients' quantities as set forth in alimentary instruction set 112, computing device 104 may remove such consumed nutrients and compare only to target nutrients and/or quantities thereof that have not yet been consumed. Computing device 104 may select each alimentary combination of plurality of alimentary combinations 124a-n by determining a nutrient listing corresponding to each alimentary combination of plurality of alimentary combinations 124a-n, creating a distance metric from the nutrient listing to the alimentary instruction set 112, and selecting at least an alimentary combination that minimizes the distance metric, and ordering 140 the plurality of alimentary combinations 124a-n according to a degree to which each alimentary combination minimizes the distance metric.

Alternatively or additionally, and still referring to FIG. 1, user and such human subjects may be matched to one another using a user classifier identifying them as mutually similar with respect to the one or more categories of data. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. User classifier may be configured to output identifiers of a bin and/or set of users identified as similar using classification algorithm, where a "identifier" is a datum that labels or otherwise identifies a user set; that is, a label identifying a set of users that have sets of user data, such as without limitation biological extractions, that are clustered together, found to be close under a distance metric as described below, or the like. A user set may be a collection of users having closely related user data regarding one or more categories for classification as described above. User classifier may include a classifier configured to input user data and output user set identifiers.

Further referring to FIG. 1, computing device 104 and/or another device may generate user classifier using a classification algorithm, defined as a processes whereby a computing device 104 derives a classifier from user classification training data. User classifier may be trained by computing device 104 and/or one or more other devices in or communicating with system 100 using training data containing a plurality of sets of data pertaining to a plurality of persons. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, plurality of elements of user data may be utilized by classification algorithms as or in training data. Training data, as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. raining data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

Still referring to FIG. 1, training data used to generate user classifier may include, without limitation, a plurality of data entries, each data entry including one or more elements of user data such as biological extractions, and one or more correlated user set identifiers, where user set identifiers and associated user data profiles may be identified using feature learning algorithms as described below. Training data and/or elements thereof may be added to, as a non-limiting example, by classification of multiple users' data to user set identifiers using one or more classification algorithms. Training data may alternatively or additionally be received in the form of one or more user inputs, for instance and without limitation from experts, operators of system, or the like. For instance identifiers used in training data may correspond to one or more categories and/or sets of data that are identified by user such as without limitation expert users as having utility and/or significance.

Alternatively or additionally, user set identifiers may be identified in a set of user data corresponding to a plurality of users by utilizing a classifier. Classifier may include, without limitation, a clustering algorithm such as a k-means clustering algorithm. A "k-means clustering algorithm" as used in this disclosure, includes cluster analysis that partitions n observations or unclassified cluster data entries into k clusters in which each observation or unclassified cluster data entry belongs to the cluster with the nearest mean, using, for instance behavioral training set as described above. "Cluster analysis" as used in this disclosure, includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster; for instance, and without limitation, a fuzzy clustering algorithm 116 may be used to identify clustering of gene combinations with multiple disease states, and vice versa. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 1, computing device 104 may generate a k-means clustering algorithm 116 receiving unclassified user data, such as without limitation biological extraction data, and outputs a definite number of classified data entry clusters wherein the data entry clusters each contain cluster data entries. K-means algorithm may select a specific number of groups or clusters to output, identified by a variable "k." Generating a k-means clustering algorithm 116 includes assigning inputs containing unclassified data to a "k-group" or "k-cluster" based on feature similarity. Centroids of k-groups or k-clusters may be utilized to generate classified data entry cluster. K-means clustering algorithm 116 may select and/or be provided "k" variable by calculating k-means clustering algorithm 116 for a range of k values and comparing results. K-means clustering algorithm 116 may compare results across different values of k as the mean distance between cluster data entries and cluster centroid. K-means clustering algorithm 116 may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering algorithm 116 may act to identify clusters of foods and/or other physiological stimuli having similar effects on a biomarker; in an embodiment, the effect may vary from one user to another, but a difference in effect for a given user from one food and/or other physiological stimulus to another food and/or physiological stimulus in the cluster may be minimal and/or small enough to cause inclusion in a cluster. In other words, two foods and/or physiological stimuli in a cluster may be expected to have similar effects to each other on a biomarker and/or set of biomarkers when received and/or consumed by a given user.

With continued reference to FIG. 1, generating a k-means clustering algorithm 116 may include generating initial estimates for k centroids which may be randomly generated or randomly selected from unclassified data input. K centroids may be utilized to define one or more clusters. K-means clustering algorithm 116 may assign unclassified data to one or more k-centroids based on the squared Euclidean distance by first performing a data assigned step of unclassified data. K-means clustering algorithm 116 may assign unclassified data to its nearest centroid based on the collection of centroids ci of centroids in set C. Unclassified data may be assigned to a cluster based on $argmin_{c_i \ni C}$ dist $(c_i, x)^2$, where argmin includes argument of the minimum, ci includes a collection of centroids in a set C, and dist includes standard Euclidean distance. K-means clustering module may then recompute centroids by taking mean of all cluster data entries assigned to a centroid's cluster. This may be calculated based on $c_i = 1/|S_i|\Sigma x_i \ni S_i^{xi}$. K-means clustering algorithm 116 may continue to repeat these calculations until a stopping criterion has been satisfied such as when cluster data entries do not change clusters, the sum of the distances have been minimized, and/or some maximum number of iterations has been reached.

Still referring to FIG. 1, k-means clustering algorithm 116 may be configured to calculate a degree of similarity index value. A "degree of similarity index value" as used in this disclosure, includes a distance measurement indicating a measurement between each data entry cluster generated by k-means clustering algorithm 116 and a selected data set. Degree of similarity index value may indicate how close an element or set of elements of user data is to being classified by k-means algorithm to a particular cluster. K-means clustering algorithm 116 may evaluate the distances of user data to the k-number of clusters output by k-means clustering algorithm 116. Short distances between a set of data regarding a food and a cluster may indicate a higher degree of similarity between the food data and a particular cluster. Longer distances between a set of data regarding a food and a cluster may indicate a lower degree of similarity between the food data and a particular cluster.

With continued reference to FIG. 1, k-means clustering algorithm 116 may select a classified data entry cluster as a function of the degree of similarity index value. In an embodiment, k-means clustering algorithm 116 may select a classified data entry cluster with the smallest degree of similarity index value indicating a high degree of similarity between user data and the data cluster. Alternatively or additionally k-means clustering algorithm 116 may select a plurality of clusters having low degree of similarity index values to user data sets, indicative of greater degrees of similarity. Degree of similarity index values may be compared to a threshold number indicating a minimal degree of relatedness suitable for inclusion of a set of food data and/or physiological stimulus data in a cluster, where degree of similarity indices falling under the threshold number may be included as indicative of high degrees of relatedness. The above-described illustration of clustering using k-means clustering is included for illustrative purposes only, and should not be construed as limiting potential implementation of clustering; persons skilled in the art, upon reviewing the entirety of this disclosure, will be aware of various additional or alternative clustering approaches that may be used consistently with this disclosure.

Still referring to FIG. 1, computing device 104 may be configured to generate user classifier using a Naïve Bayes classification algorithm. Naïve Bayes classification algorithm generates classifiers by assigning class labels to problem instances, represented as vectors of element values. Class labels are drawn from a finite set. Naive Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naive Bayes algorithm may be generated by first transforming training data into a frequency table. Computing device 104 may then calculate a likelihood table by calculating probabilities of different data entries and classification labels. Computing device 104 may utilize a naive Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate user classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting example, K-nearest neighbors algorithm may be configured to classify an input vector including a plurality of user data to vectors representing similar users' data.

Still referring to FIG. 1, a "distance metric 144," as used in this disclosure, is a quantitative value indicating a degree of similarity of a set of data values to another set of data values. For instance, and without limitation, combinations of nutrient quantities associated with each ingredient combination, and target nutrient quantities 116 of alimentary instruction set 112, may be represented a vector. Each vector may be represented, without limitation, as an n-tuple of values, where n is at least two values. Each value of n-tuple of values may represent a measurement or other quantitative value associated with a given category of data, or attribute, such as a nutrients, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. A non-limiting distance metric 144 may include a degree of vector similarity. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent, for instance as measured using cosine similarity; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l = \sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting illustration, target nutrients from alimentary instruction set 112, and/or one or more subsets thereof, may be represented using a vector or other data structure, and nutrients provided by each ingredient combination of plurality of ingredient combinations may be represented by a like data structure, such as another vector; a distance metric 144 comparing the two data structures may then be calculated and compared to distance metric 144s calculations to find a minimal distance metric 144 calculation and/or a set of minimal distance metric 144 calculations. A set of minimal distance metric 144 calculations may be a set of distance metric 144 calculations less than a preconfigured threshold distance from data structure representing target nutrients. Preconfigured threshold may be set by one or more expert users and/or determined statistically, for instance by finding a top quartile and/or number of percentiles of proximity in a series of distance metric 144 determinations over time for user, at one time for a plurality of users, and/or over time for a plurality of users. Plurality of users may include a plurality of users selected by a user classifier, which may classify user to a plurality of users having similar physiological data and/or user data; implementation of a user classifier may be performed, without limitation, as described in U.S. Nonprovisional application Ser. No. 16/865,740, filed on May 4, 2020 and entitled "METHODS AND SYSTEMS FOR SYSTEM FOR NUTRITIONAL RECOMMENDATION USING ARTIFICIAL INTELLIGENCE ANALYSIS OF IMMUNE IMPACTS," the entirety of which is incorporated herein by reference.

Alternatively or additionally, selecting the at least an alimentary combination may include generating a distance metric 144 from each alimentary combination of the plurality of alimentary combinations 124a-n to ingredient combinations specified in alimentary instruction set 112; such beneficial ingredient combinations of the plurality of beneficial ingredient combinations may be generated by a classifier or other process for identifying ingredient combinations that accomplish nutritional purposes of alimentary instruction set 112.

With continued reference to FIG. 1, distance metric 144 may be performed using a loss function analysis. In an embodiment, computing device 104 may compare one or more alimentary and/or non-alimentary data to a mathematical expression representing a plurality of alimentary instruction set 112 quantities and/or non-alimentary ordering 140 criteria. Mathematical expression may include a linear combination of variables, weighted by coefficients representing relative importance of each non-alimentary ordering 140 criterion. For instance, a variable such as food quality, importance to user of organic ingredients versus nonorganic ingredients may be multiplied by a first coefficient representing the importance of organic food standards, a second user input such as total cost may be multiplied by a second coefficient representing the importance of cost, a degree of variance from alimentary instruction set 112 nutrient quantities and/or beneficial ingredient sets may be represented as another parameter, which may be multiplied by another coefficient representing the importance of that parameter, a degree of variance from a preference for fresh or frozen ingredients may be multiplied by an additional coefficient representing an importance of that parameter, or the like; persons skilled in the art, upon reviewing the entirety of this disclosure, will be aware of different variables that may be weighted by various coefficients. Use of a linear combination is provided only as an illustrative example; other mathematical expressions may alternatively or additionally be used, including without limitation higher-order polynomial expressions or the like.

Still viewing FIG. 1, mathematical expression may represent a loss function, where a "loss function" is an expression an output of which an optimization algorithm minimizes to generate an optimal result. As a non-limiting example, computing device 104 may calculate variables of set of provider parameters and/or variance of such parameters from non-alimentary ordering 140 criteria calculate an output of mathematical expression using the variables, and select candidate ingredient combination that produces an output having the lowest size, according to a given definition of "size," of the set of outputs representing each of plurality of candidate ingredient combinations; size may, for instance, included absolute value, numerical size, or the like. Selection of different loss functions may result in identification of different candidate ingredient combinations as generating minimal outputs; for instance, where organic ingredients is associated in a first loss function with a large coefficient or weight, a candidate ingredient combination having a small coefficient or weight for organic ingredients may minimize the first loss function, whereas a second loss function wherein organic ingredients has a smaller coefficient but degree of variance from cost goal which has a larger coefficient may produce a minimal output for a different candidate ingredient combination having a larger organic ingredients but more closely hewing to a cost goal.

Alternatively or additionally, and still referring to FIG. 1, each candidate ingredient combination may be represented by a mathematical expression having the same form as mathematical expression; computing device 104 may compare the former to the latter using an error function representing average difference between the two mathematical expressions. Error function may, as a non-limiting example, be calculated using the average difference between coefficients corresponding to each parameter. A candidate ingredient combination having a mathematical expression minimizing the error function may be selected, as representing an optimal expression of relative importance of parameters to a system or user. In an embodiment, error function and loss function calculations may be combined; for instance, a candidate ingredient combination resulting in a minimal aggregate expression of error function and loss function, such as a simple addition, arithmetic mean, or the like of the error function with the loss function, may be selected, corresponding to an option that minimizes total variance from non-alimentary ordering 140 criteria while simultaneously minimizing a degree of variance from a set of priorities corresponding to non-alimentary ordering 140 criteria. Coefficients of mathematical expression and/or loss function may be scaled and/or normalized; this may permit comparison and/or error function calculation to be performed without skewing by varied absolute quantities of numbers.

In an embodiment, and further referring to FIG. 1, neutral ingredients and/or neutral nutrients may be excluded from data structures used in distance metric 144 calculations as described in this disclosure. A "neutral ingredient" as used in this disclosure is an ingredient that has not been determined to have a measurable negative or positive effect on constitution of a person, such as some seasonings, spices, or the like. In an embodiment, system 100 may not map neutral ingredients to nutrients; for instance, ingredient nutrient datastore 136 may not list nutrients for a neutral ingredient. Alternatively or additionally a nutrient having no measurable positive or negative constitutional effect, referred to for purposes of this disclosure as a "neutral nutrient," may be listed in ingredient nutrient datastore 136, but excluded from distance metric 144 calculations. As a non-limiting example, two foods having ingredients differing only by neutral ingredients and/or neutral nutrients may thus be treated by system 100 as equivalent.

Alternatively or additionally, graphical user interface 120 may utilize a combination of pieces of alimentary and/or non-alimentary data, which may be weighted, to rank an alimentary ingredient combination across a plurality of alimentary providers. For instance, graphical user interface 120 may rank a given dish from a given alimentary provider by computing a weight corresponding to a cost of the dish at the alimentary provider, a weight corresponding to a rating of the cost at the alimentary provider, and a weight corresponding to a distance from and/or degree of compliance with alimentary instruction set 112, and multiplying one or more weighting factors times a base ranking and/or times each other. Weighting factors may be based on user preferences, which may, for instance, be entered as described in further detail below. The above methods may be combined; for instance, a distance metric 144 may be computed first with regard to alimentary data only, creating a variable produced thereby which is used with one coefficient in a loss function and/or with one weighting factor in a weighted ranking process to produce an ordering 140 incorporating non-alimentary data.

Attributes used in distance metric 144, loss functions, weightings, or the like may be normalized across geographical regions, time periods, or the like. A geographical region may be defined from a boundary of a city, county, state, country, and so on. Alternatively, a geographical region may be defined from a geo-fence around a user. For instance, and without limitation, graphical user interface 120 may determine a range of costs at which an alimentary combination is purveyed within a geographical region. Graphical user interface 120 may then divide the range of the costs into sub-ranges of costs. Offerings of alimentary combination may be ranked and/or ordered according to the sub-ranges.

Figure 2:
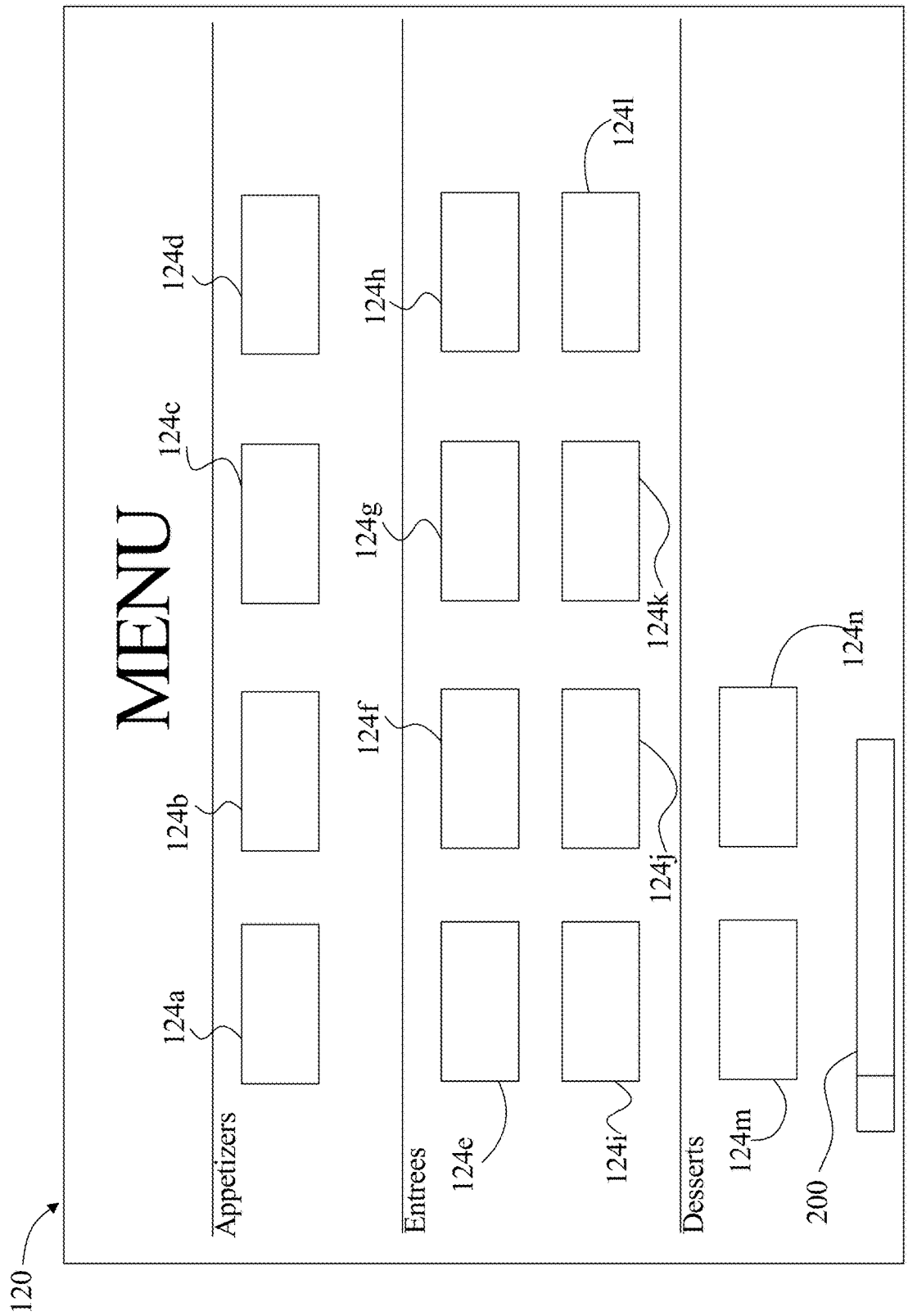
FIG. 2 is a schematic diagram of an exemplary embodiment of a graphical user interface.
Figure 3:
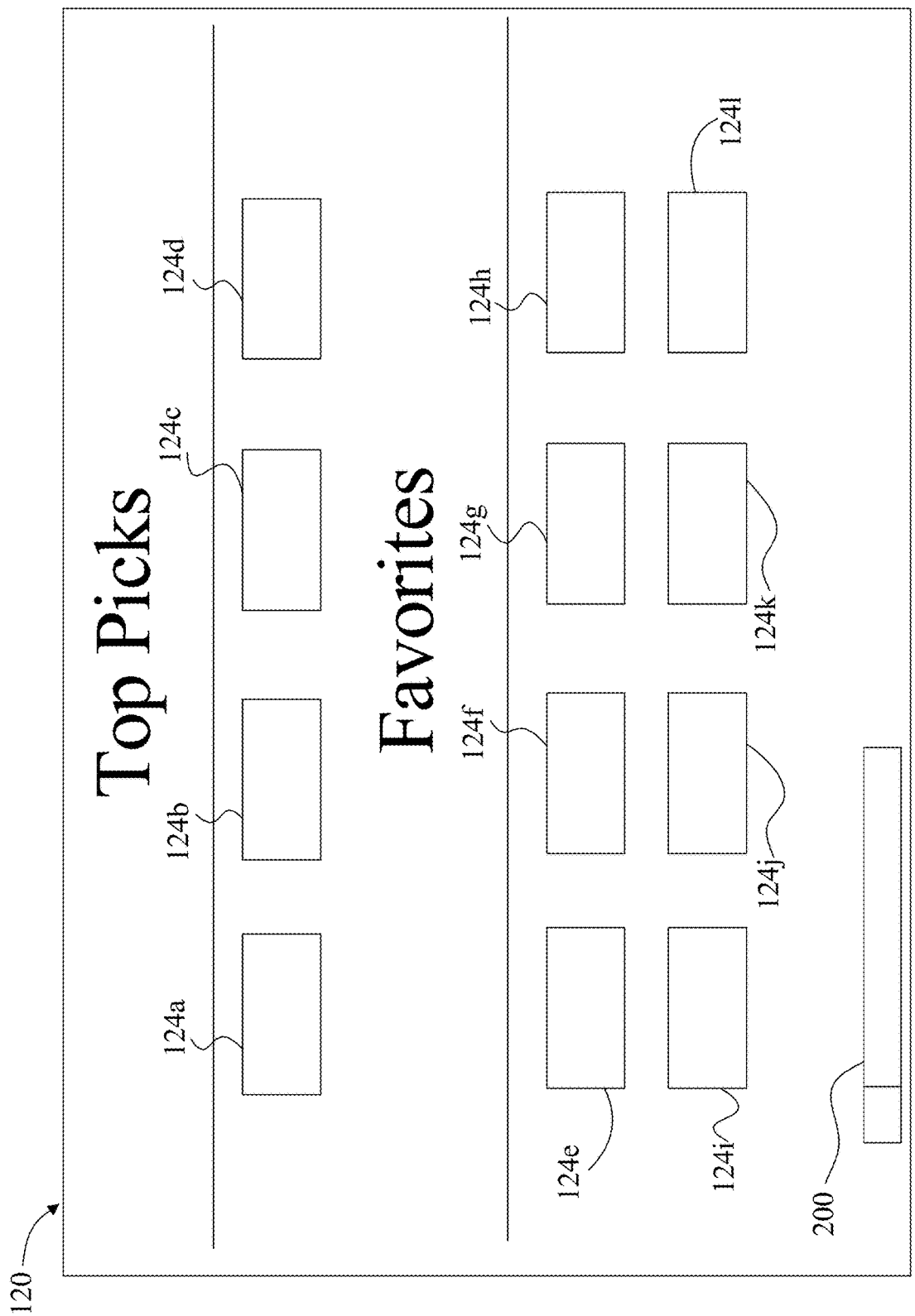
FIG. 3 is a schematic diagram of an exemplary embodiment of a graphical user interface.

Referring now to FIG. 2, an exemplary embodiment of a graphical user interface 120 is illustrated. In an embodiment, graphical user interface 120 may display a plurality of alimentary combinations 124a-n from a single alimentary provider device 128a-n and/or alimentary provider. For instance, and without limitation, graphical user interface 120 may function to generate a menu that places alimentary combinations 124a-n in the order corresponding to the ordering 140. Graphical user interface 120 may cause client device 108 to display on client device 108 when client device 108 is visiting and/or rendering a website of alimentary provider in a web browser and/or application; for instance, graphical user interface 120 may display on client device 108 embedded within a display of data from website, for instance in the form of an embedded frame and/or a page within website. Embedding may occur in website either at alimentary provider device 128a-n or at client device 108; that is, graphical user interface 120 may be transmitted to alimentary provider device 128a-n, and thence to client device 108 with the remainder of internet page or may be transmitted to client device 108 and embedded within internet page using a client-side program transmitted to client device 108. Alimentary combinations 124a-n may be displayed in graphical user interface 120 in order of ordering 140, such as in a rank-ordered list. Alternatively or additionally, alimentary combinations 124a-n may be displayed according to one or more categories such as without limitation appetizers, entrees, sandwiches, desserts, beverages, types of preparation, principal ingredients such as beef, seafood, vegetarian, or the like, times of availability, or any other categorization according to which a menu and/or items thereof may be displayed that may occur to persons skilled in the art upon reviewing the entirety of this disclosure; ordering 140 may be used to order display within categories. Alternatively or additionally, distance metric 144 and/or other ranking of each alimentary combination may be compared to a preconfigured threshold, which may be in the form of a stored numerical quantity or set thereof, and only alimentary combinations 124a-n satisfying the preconfigured threshold, such as by having a distance metric 144 falling below the threshold, a ranking exceeding the threshold, or the like, may be displayed. Graphical user interface 120 may include one or more user inputs 200, which may permit a user of client device 108 to set priority inputs and/or filtering criterion as set forth in further detail below. In an embodiment, graphical user interface 120 and/or computing device 104 may track previous user data entries, selections of displayed options, and/or selections and/or orders of alimentary combinations 124a-n. Such selections may be used in training data for generation of loss function as described above and/or to set default priority inputs as described in further detail below. Referring now to FIG. 3, an exemplary embodiment of a graphical user interface 120 is illustrated. In an embodiment, graphical user interface 120 may display alimentary combinations 124a-n offered by a plurality of alimentary providers. In an embodiment, a user may be able to toggle between a provider-specific view in graphical user interface 120, for instance as illustrated in FIG. 2, and a multi-provider view, for instance as illustrated in FIG. 3; toggling may be accomplished by user entry of a name of a specific provider in a search field, selection thereof from a drop-down list or other listing of providers, for instance within a geographical area, according to one or more categories and/or genres of provider and/or food, or the like, and/or by selecting a link or other event-handling display element associated with an alimentary combination offered by the provider. Any form of display according to ordering 140 as described above in FIG. 2 may be employed in FIG. 3, including without limitation rank-ordered display, display according to categories, threshold-based elimination, or the like. Categories may further include genres such as regional cuisines and/or cuisine styles, different individual providers, or the like. Such ordering 140 performed with regard to multiple alimentary providers may have an effect of sorting displayed alimentary combinations 124a-n as ranked according to ordering 140, as well as ranking of providers and/or alimentary combinations 124a-n thereof across genres, within a given geographical region, or the like. Display may include, for instance, obtaining each alimentary provider's highest-ranking alimentary combination per category displayed, comparing to a threshold for display selection, and/or displaying according to any rank order as described above. User inputs 200 may select categories for display as well as priority inputs and/or other criteria. Thus, as a non-limiting example, a user may input data indicating a desire to see all offerings of Indian restaurants within a five-mile radius of user that is available for delivery within a half hour; graphical user interface 120 may display alimentary combinations 124a-n offered thereby as consistent with the above-described criteria, and displayed in any manner suitable for categorization and rank-ordering 140 as described above. Alternatively or additionally, previously recorded user preferences may be used to set initial display criteria, which may be overridden and/or modified by subsequent user inputs.

Still referring to FIG. 3, generation of ordering 140 may be performed on client device 108, by performing distance metric 144 computations and assigning orderings 140 on client device 108 as described above and/or by receiving distance metric 144 computations and/or other ordering 140 assignments per alimentary combination from computing device 104 and/or alimentary processing device and associating such distance metric 144s and/or ordering 140 assignments with alimentary combinations 124a-n as received. Alternatively or additionally, ordering 140 may be performed in a combination of the above-described approaches; for instance, ordering 140 per provider may be performed on alimentary provider device 128a-n, and overall ordering 140 on computing device 104 and/or client device 108. As a further non-limiting example, any ordering 140 may be initially received from computing device 104 and/or alimentary provider device 128a-n, and then may be subsequently reordered on user device per user instructions. As noted above, one or more orderings 140, whether received or generated on client device 108 may be stored by graphical user interface 120 locally to client device 108 for deployment in response to one or more user entries.

In an embodiment, and still referring to FIG. 3, graphical user interface 120 may configure user device to receive a plurality of non-alimentary data. "non-alimentary data," as used in this disclosure is any data besides nutrient quantities and/or ingredients as described above. non-alimentary data may include, without limitation, user profile data such as previously recorded preferences and/or previously recorded user selections, names of dishes, styles of dishes, prices or other costs, one or more temporal elements such as a preparation time for an alimentary provider to prepare an alimentary combination a courier time for a courier to transport an alimentary combination to a current geographical location of a user, an amount of time to obtain ingredients for alimentary combination, an amount of time to obtain additional ingredients, and/or any combination thereof for instance to obtain a total time to receive an alimentary combination, ratings by customers, ratings by professional reviewers, and/or any other element of data according to which a person or machine may distinguish one alimentary combination from another, aside from alimentary data as described above.

With continued reference to FIG. 3, plurality of non-alimentary data may include, without limitation, at least a non-alimentary datum associated with each alimentary combination of the plurality of alimentary combinations 124a-n. For instance and without limitation, alimentary provider device 128a-n, graphical user interface 120, and/or computing device 104 may associate a price, preparation time, time to delivery, customer rating, or a datum corresponding to any other category of non-alimentary data with each alimentary combination; association of data in a given category with each alimentary combination may enable graphical user interface 120 to use ordering 140 to compare like data across alimentary combinations 124a-n. Association may be performed by alimentary provider device 128a-n, graphical user interface 120, and/or computing device 104. Graphical user interface 120 may configure user device to receive plurality of non-alimentary data from at least a third-party remote device, such as without limitation a device operated by a courier. A "courier," as used herein, is a person or service that delivers or transports alimentary combinations 124a-n. For example, a courier may deliver an alimentary combination from one location of a town to another location of a town, from one city to another city, from one state to another state, and so on. As such, a courier may include a network of couriers that each handle delivery for a specific region. Delivery of an alimentary combination to a destination may include a transfer thereof from one courier to another courier. A courier may include a company that is dedicated to delivering alimentary combinations 124a-n or a company that is primarily dedicated to other services but includes some courier services. In some instances, a courier may be associated with and/or a part of an alimentary provider, while in other instances the courier may be independent of the alimentary provider. A plurality of couriers may be available to transport alimentary combinations 124a-n from a given alimentary provider; in this case, system 100 may obtain delivery times from each courier and determine a minimal currently available delivery time by comparison thereof, and/or may determine a location of each courier and determine a likely delivery time as a function of likely transit time from current location to alimentary provider and/or user of client device 108. In yet other examples, courier may be a customer that delivers an item for another customer. As a non-limiting example, a delivery estimation may be based on historical data, such as a previous amount of preparation time that was taken to prepare an alimentary combination, a previous amount of courier time that was taken to transport an item, an average of previous preparation times or previous courier times, or the like. A delivery estimation may be determined from a current location of a courier. In some instances, the alimentary provider device 128a-n and/or computing device 104 may collect location information from a courier indicating a current location of an electronic device associated with the courier; this may allow the alimentary provider device 128a-n to track a location of the courier to determine when the courier has delivered an alimentary combination, determine a route that is traveled by the courier, determine an amount of time to deliver an alimentary combination, and the like. Delivery estimation may further depend on traffic conditions for a geographical region or route, such as traffic conditions along a route from a current location of a courier to an alimentary provider (e.g., to retrieve an alimentary combination), traffic conditions along a route from an alimentary provider to a current location of a user, or the like.

Still referring to FIG. 3, graphical user interface 120 may configure user device to receive plurality of non-alimentary data from at least an alimentary provider device 128a-n. Computing device 104 may, for instance, receive from alimentary provider device 128a-ns, values corresponding to any or all categories of non-alimentary ordering 140 data and/or criteria as described above.

Still referring to FIG. 3, graphical user interface 120 may configure user device to generate the ordering 140 using the plurality of non-alimentary data. For instance and without limitation, distance metric 144 may measure each alimentary combination and at least a non-alimentary datum against a plurality of target nutrient quantities 116 and at least a non-alimentary ordering 140 criterion. Graphical user interface 120 may be configured to receive at least a non-alimentary ordering 140 criterion from client device 108. Computing device 104 may perform selection by identifying one or more non-alimentary ordering 140 criteria and selecting utilizing the one or more non-alimentary ordering 140 criteria. As used in this disclosure, a "non-alimentary ordering 140 criterion" is a datum setting a desired quantity of a non-alimentary datum, for instance as a user preference with respect to such a non-alimentary datum. A non-alimentary ordering 140 criterion may include, any element of data suitable for use as a non-alimentary datum, including without limitation, a time of delivery of a candidate ingredient combination, an amount of time to prepare a candidate ingredient combination, an identity of a dish to be prepared using candidate ingredient combination, a cost of candidate ingredient combination such as a cost to be paid to a user, a cost of delivery, a delivery transit time, and/or a rating such as a quantitative rating of a preparer such as a chef, a quantitative rating of the dish, a quantitative rating of the alimentary provider, a quantitative rating of a delivery service, or the like. Qualitative ratings may include customer ratings collected using customer satisfaction surveys, expert ratings by reviewers, or the like.

Still referring to FIG. 1, at least a non-alimentary ordering 140 criterion may include at least a default parameter; for instance, as a default, computing device 104 may set as non-alimentary ordering 140 criterion a minimal cost, a delivery time below a certain threshold, and maximal qualitative ratings for one or more aspects of delivery. Alternatively or additionally, computing device 104 may receive at least a user parameter and select at least a recommended ingredient combination from the plurality of candidate ingredient combinations to match the at least a user parameter; user parameter may, for instance be added to and/or used to modify at least a default non-alimentary ordering 140 criterion. For instance, user may set as a non-alimentary ordering 140 criterion a particular dish the user is interested in consuming; user may select the dish, for instance and without limitation by being provided a list of dishes representing beneficial ingredient combinations, e.g. by being composed of ingredients of a beneficial ingredient combination, and selecting one displayed dish. User may set a particular price range, a particular delivery time and/or duration, or the like that interests the user. User may also provide inputs describing relative importance to user of each non-alimentary ordering 140 criterion, whether set by system 100 or user entered.

Still referring to FIG. 3, a mathematical expression and/or loss function used in distance metric 144 calculation may be provided by receiving inputs, such as user inputs, indicating relative importance of data used for distance metric 144 calculations. For instance, and without limitation, graphical user interface 120 may be configured to receive, from client device 108, at least a priority input, defined as one or more user commands specifying non-alimentary criteria, and to configure the client device 108 to generate ordering 140 as a function of the at least a priority input. For instance, and without limitation, a graphical user interface 120 may be provided to user with a set of sliders or other user inputs permitting a user to indicate relative and/or absolute importance of each parameter to the user. Sliders or other inputs may be initialized prior to user entry as equal or may be set to default values based on results of any machine-learning processes or combinations thereof as described in further detail below. Priority inputs may alternatively or additionally be set by aggregating data previously entered and/or selected based on previous user inputs and, for instance, calculating average values and/or using regression to generate loss functions as described above. Entry of priority inputs may also include an indication by user of which criteria should be used in distance metric 144 calculation or the like; user may select only a subset of criteria according to which to calculate distance metric 144 and/or ordering 140 process. For instance, user may request a ranking and/or ordering 140 according to delivery time, delivery time and cost, a combination of delivery time, cost, and customer rating, and so forth.

With continued reference to FIG. 3, mathematical expression and/or loss function may be generated using a machine learning to produce loss function, such as without limitation using a regression algorithm. Mathematical expression and/or loss function may be user-specific, using a training set composed of past user selections; mathematical expression and/or loss function may be updated continuously. Mathematical expression and/or loss function may initially be seeded using one or more user entries as above. User may enter a new command changing mathematical expression, and then subsequent user selections may be used to generate a new training set to modify the new expression.

With continued reference to FIG. 3, mathematical expression and/or loss function may be generated using machine learning using a multi-user training set. Training set may be created using data of a cohort of persons having similar demographic, religious, constitutional, and/or lifestyle characteristics to user. This may alternatively or additionally be used to seed a mathematical expression and/or loss function for a user, which may be modified by further machine learning and/or regression using subsequent user selections of candidate ingredient combinations. Use of regression to derive loss functions, loss function coefficients, and/or mathematical expressions may be performed, without limitation, as described in U.S. Nonprovisional application Ser. No. 16/502,835.

Still referring to FIG. 3, graphical user interface 120 configures client device 108 to display at least an alimentary combination of the plurality of alimentary combinations 124*a-n* using ordering 140. This may be accomplished using any process described above, including without limitation display of elements for a single alimentary provider and/or multiple alimentary providers, display by categories, rank-ordering 140 and/or threshold comparison. Graphical user interface 120 may further provide user with data entry fields as described above for entry of one or more filtering criteria; graphical user interface 120 may display only alimentary combinations 124*a-n* matching the one or more filtering criteria. For instance, if user is searching for pizza, only pizza options may be displayed, if user is searching for alimentary providers within 5 miles of user, those farther may be eliminated from display, and so forth.

Still referring to FIG. 3, display may include one or more additional elements and/or fields to illustrate displayed data. Such elements may include, without limitation, a map having a visual representation for each of the identified alimentary providers located at an establishment thereof. Each visual representation may indicate one or more elements of data such as a ranking of the alimentary provider and/or of an alimentary combination associated therewith which may be selected for display according to any criterion or combination of criteria described above. Graphical user interface 120 may provide user a button or other display element usable to order an alimentary combination electronically, along with, for instance, fields for special instructions or the like. User location may be automatically detected and included with order, or user may specify a location for delivery.

Figure 4:
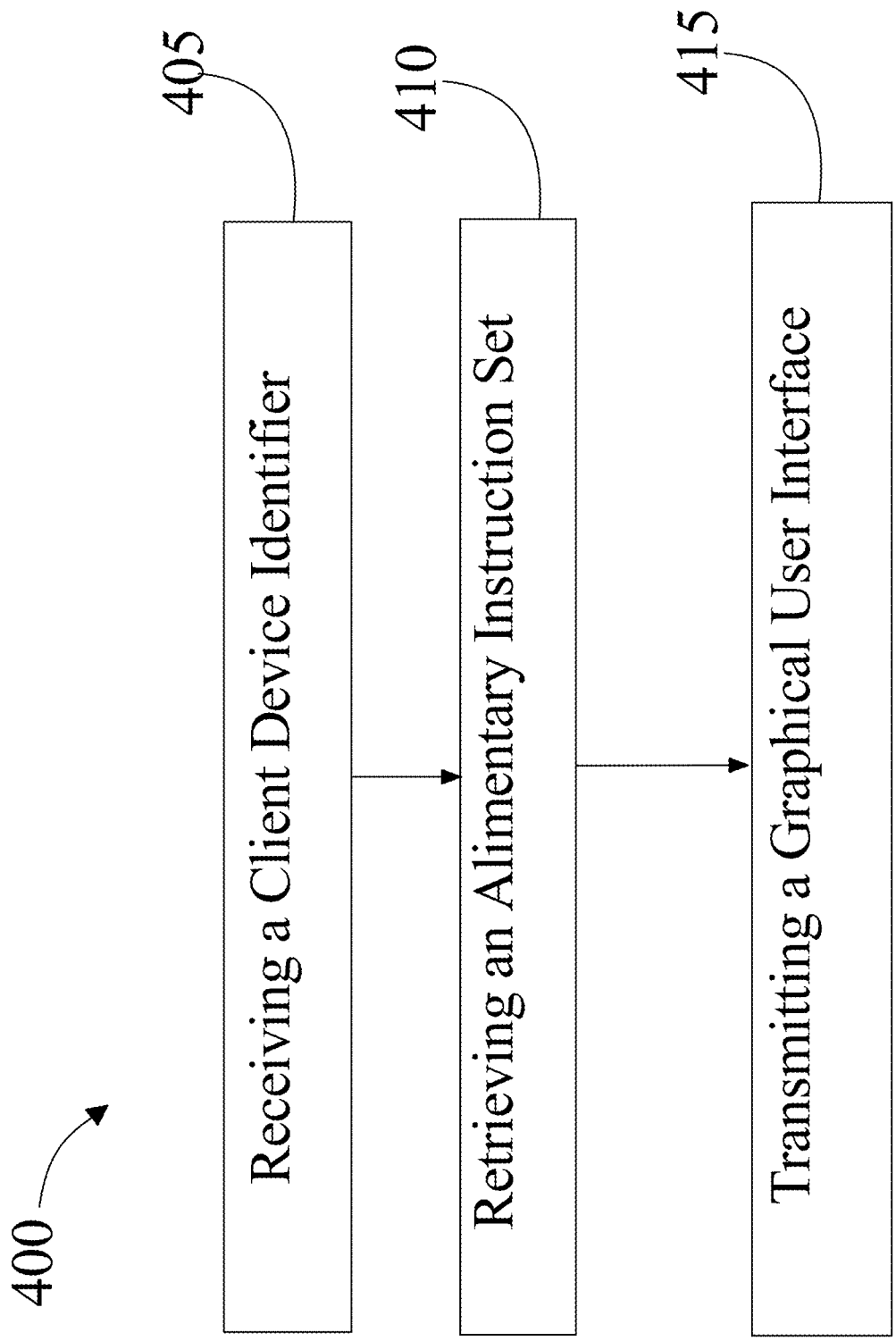
FIG. 4 is a flow diagram of an exemplary embodiment of a method of providing alimentary combinations in a packet-based graphical user interface generated using distance metric.

Referring now to FIG. 4, an exemplary embodiment of a method 400 of providing alimentary combinations 124*a-n* in a packet-based graphical user interface 120 generated using distance metric 144s is illustrated. At step 405, a computing device 104 receives a client device identifier; this may be implemented, without limitation, as described above in reference to FIGS. 1-3.

At step 410, retrieving, as a function of the client device identifier, an alimentary instruction set 112 including a plurality of target nutrient quantities 116; this may be implemented, without limitation, as described above in reference to FIGS. 1-3.

At step 415, transmitting a graphical user interface 120 to a client device 108 using an electronic transmission protocol, the graphical interface configured to cause a user device to display a plurality of alimentary combinations 124*a-n*; this may be implemented, without limitation, as described above in reference to FIGS. 1-3. Transmitting graphical user interface 120 to client device 108 may include remotely configuring the at least an alimentary provider device 128*a-n* to transmit the graphical user interface 120 to the client device 108. Graphical user interface 120 configures client device 108 to receive, from at least an alimentary provider device 128*a-n*, a plurality of alimentary combinations 124*a-n*, for instance as described above in reference to FIGS. 1-3. For instance, graphical user interface 120 may configure client device 108 to receive plurality of alimentary combinations 124*a-n* from alimentary provider device 128*a-n* through the computing device 104. At least an alimentary provider device 128*a-n* may include a plurality of alimentary provider device 128*a-ns*. Graphical interface configures client device 108 to generate an ordering 140 of the plurality of alimentary combinations 124*a-n* according to a distance metric 144 measuring each alimentary combination against the plurality of target nutrient quantities 116, for instance as described above in reference to FIGS. 1-3.

Still referring to FIG. 4, graphical user interface 120 may configure user device to receive a plurality of non-alimentary data, the plurality of non-alimentary data including at least a non-alimentary datum associated with each alimentary combination of the plurality of alimentary combinations 124*a-n*, and generate the ordering 140 using the plurality of non-alimentary data. Graphical user interface 120 may configure user device to receive plurality of non-alimentary data from at least a third-party remote device. Graphical user interface 120 may configure user device to receive plurality of non-alimentary data from at least an alimentary provider device 128*a-n*. Distance metric 144 may measure each alimentary combination and at least a non-alimentary datum against a plurality of target nutrient quantities 116 and at least a non-alimentary ordering 140 criterion. Graphical user interface 120 may be configured to receive at least a non-alimentary ordering 140 criterion from client device 108. Graphical user interface 120 may be configured to receive, from client device 108, at least a priority input, and to configure the client device 108 to generate ordering 140 as a function of the at least a priority input.

Still referring to FIG. 4, graphical user interface 120 configures client device 108 to display at least an alimentary combination of the plurality of alimentary combinations 124*a-n* using the ordering 140; this may be implemented, without limitation, as described above in reference to FIGS. 1-3.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 5:
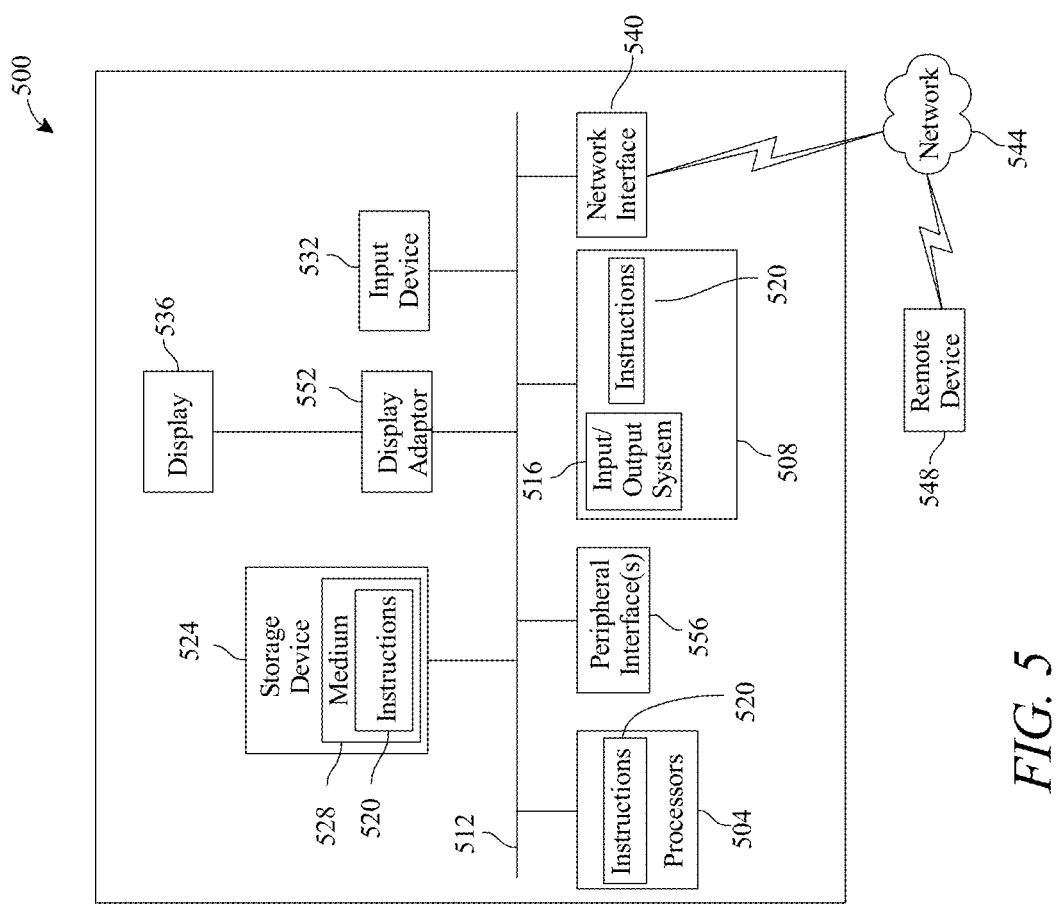
FIG. 5 is a block diagram of a computing system that can be used to implement any one or more of the methodologies disclosed herein and any one or more portions thereof.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Processor 504 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 504 may be organized according to Von Neumann and/or Harvard architecture as a non-limiting example. Processor 504 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 508 may include various components (e.g., machine-readable media) including, but not limited to, a random-access memory component, a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor 504.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote devices 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering 140 is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for providing alimentary combinations in a packet-based graphical user interface generated using distance metrics, the system comprising a computing device designed and configured to:
   receive user classification training data, wherein the user classification training data includes a plurality of elements correlating user data entries to user set identifiers;
   receive at least an element of user data;
   train a user classifier as a function of the user classification training data using a machine learning algorithm;
   classify the at least an element of user data to a user set identifier;
   set a non-alimentary ordering criterion default parameter as a function of the user set identifier; and
   order an alimentary combination as a function of the non-alimentary ordering criterion and a computed distance metric, wherein ordering associates each alimentary combination with a quantity that reflects a degree to which the alimentary combination satisfies a target nutrient quantity.

2. The system of claim 1, wherein the user classifier is trained using a Naïve Bayes classification algorithm.

3. The system of claim 1, wherein the user classifier is trained using a K-nearest neighbors' algorithm.

4. The system of claim 1, wherein the system is further configured to set default alimentary providers as a function of the non-alimentary ordering criterion.

5. The system of claim 4, wherein the system is further configured to receive alimentary ingredient combinations from default alimentary providers as a function of the non-alimentary ordering criterion.

6. The system of claim 5, wherein the system is further configured to set default target nutrient quantities of the alimentary ingredient combinations as a function of the non-alimentary ordering criterion.

7. The system of claim 1, wherein the system is further configured to transmit a default graphical user interface to a client device as a function of the non-alimentary ordering criterion.

8. The system of claim 7, wherein the default graphical user interface is set as an initial page on the client device.

9. The system of claim 1, wherein the system is further configured to modify the non-alimentary ordering criterion default parameter as a function of a user input.

10. The system of claim 9, wherein the system is further configured to delete the non-alimentary ordering criterion default parameter as a function of a user input.

11. A method of providing alimentary combinations in a packet-based graphical user interface generated using distance metrics, the method comprising:
    receiving, by computing device, user classification training data, wherein the user classification training data includes a plurality of elements correlating user data entries to user set identifiers;
    receiving, by the computing device, at least an element of user data;
    training, by the computing device, a user classifier as a function of the user classification training data using a machine learning algorithm;
    classifying the at least an element of user data to a user set identifier;
    setting, by the computing device, a non-alimentary ordering criterion default parameter as a function of the user set identifier; and
    ordering, by the computing device, an alimentary combination as a function of the non-alimentary ordering criterion and a computed distance metric, wherein ordering associates each alimentary combination with a quantity that reflects a degree to which the alimentary combination satisfies a target nutrient quantity.

12. The method of claim 11, wherein the user classifier is trained using a Naïve Bayes classification algorithm.

13. The method of claim 11, wherein the user classifier is trained using a K-nearest neighbors' algorithm.

14. The method of claim 11, wherein setting default alimentary providers is performed as a function of the non-alimentary ordering criterion.

15. The method of claim 14, wherein receiving alimentary ingredient combinations from default alimentary providers is performed as a function of the non-alimentary ordering criterion.

16. The method of claim 15, wherein setting default target nutrient quantities of the alimentary ingredient combinations is performed as a function of the non-alimentary ordering criterion.

17. The method of claim 11, wherein a default graphical user interface is transmitted to a client device as a function of the non-alimentary ordering criterion.

18. The method of claim 17, wherein the default graphical user interface is set as an initial page on the client device.

19. The method of claim 11, wherein the non-alimentary ordering criterion default parameter is modified as a function of a user input.

20. The method of claim 19, wherein the non-alimentary ordering criterion default parameter is deleted as a function of a user input.

\* \* \* \* \*